United States Patent
Knebel et al.

(10) Patent No.: US 9,030,734 B2
(45) Date of Patent: May 12, 2015

(54) SCANNING MICROSCOPE, AND METHOD FOR LIGHT MICROSCOPY IMAGING OF A SPECIMEN

(75) Inventors: Werner Knebel, Kronau (DE); Arnold Giske, Heidelberg (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 0 days.

(21) Appl. No.: 13/978,165

(22) PCT Filed: Feb. 20, 2012

(86) PCT No.: PCT/EP2012/052863
§ 371 (c)(1),
(2), (4) Date: Sep. 6, 2013

(87) PCT Pub. No.: WO2012/113752
PCT Pub. Date: Aug. 30, 2012

(65) Prior Publication Data
US 2013/0335818 A1 Dec. 19, 2013

(30) Foreign Application Priority Data

Feb. 21, 2011 (DE) .......................... 10 2011 000 835

(51) Int. Cl.
*G02B 21/06* (2006.01)
*G02B 26/08* (2006.01)
(Continued)

(52) U.S. Cl.
CPC ............ *G02B 21/06* (2013.01); *G01N 21/6458* (2013.01); *G02B 21/0032* (2013.01); *G02B 21/006* (2013.01); *G02B 21/0076* (2013.01)

(58) Field of Classification Search
USPC .................. 359/368, 385, 389, 213.1; 348/79
See application file for complete search history.

(56) References Cited

U.S. PATENT DOCUMENTS 5,952,668 A    9/1999  Baer
8,084,754 B2  12/2011  Hell et al.
(Continued)

FOREIGN PATENT DOCUMENTS

DE          44 16 558 C2     9/1997
DE    10 2005 027 077 A1     5/2006
(Continued)

OTHER PUBLICATIONS

A. H. Voie et al., "Orthogonal-Plane Fluorescence Optical Sectioning: Three-Dimensional Imaging of Macroscopic Biological Specimens", Journal of Microscopy, Jun. 1993, pp. 229-236, vol. 170, Pt. 3.

(Continued)

*Primary Examiner* — Scott J Sugarman
*Assistant Examiner* — Mustak Choudhury
(74) *Attorney, Agent, or Firm* — Crowell & Moring LLP

(57) ABSTRACT

A scanning microscope is described, having an illumination unit for emitting an illumination light beam, an objective for generating an elongated illumination focus in a specimen to be imaged, and a scanning apparatus for moving the illumination focus over a target region of the specimen to be illuminated by modifying the direction of incidence in which the illumination light beam is incident into an entrance pupil of the objective. The scanning apparatus directs the illumination light beam onto a sub-region of the entrance pupil offset from the pupil center in order to incline the illumination focus relative to the optical axis of the objective, and modifies the direction of incidence of the illumination light beam within that sub-region in order to move the illumination focus over the target region to be illuminated.

20 Claims, 8 Drawing Sheets

(51) Int. Cl.
*G02B 26/10* (2006.01)
*G02B 26/12* (2006.01)
*G01N 21/64* (2006.01)
*G02B 21/00* (2006.01)

(56) References Cited

U.S. PATENT DOCUMENTS

| | | | |
|---|---|---|---|
| 2002/0109101 A1* | 8/2002 | Hoffmann | 250/458.1 |
| 2008/0032414 A1 | 2/2008 | Zhuang et al. | |
| 2009/0134342 A1 | 5/2009 | Hell et al. | |
| 2009/0237765 A1* | 9/2009 | Lippert et al. | 359/213.1 |
| 2010/0067102 A1 | 3/2010 | Yokoi et al. | |
| 2011/0134521 A1* | 6/2011 | Truong et al. | 359/388 |
| 2013/0094755 A1 | 4/2013 | Lippert et al. | |

FOREIGN PATENT DOCUMENTS

| | | |
|---|---|---|
| DE | 10 2005 007 756 A1 | 8/2006 |
| DE | 10 2006 021 317 B3 | 10/2007 |
| DE | 10 2007 045 897 A1 | 4/2009 |
| DE | 10 2008 019 957 A1 | 11/2009 |
| DE | 10 2008 024 568 A1 | 12/2009 |
| JP | 2005-3909 A | 1/2005 |
| JP | 2005-140925 A | 6/2005 |
| JP | 2009-229715 A | 10/2009 |
| JP | 2010-15026 A | 1/2010 |
| JP | 2010-92002 A | 4/2010 |
| WO | WO 2006/127692 A2 | 11/2006 |
| WO | WO 2007/128434 A1 | 11/2007 |
| WO | WO 2010/012980 A1 | 2/2010 |

OTHER PUBLICATIONS

Jan Huisken et al., "Optical Sectioning Deep Inside Live Embryos by Selective Plane Illumination Microscopy", Science, Aug. 13, 2004, pp. 1007-1009, vol. 305.
F. Fahrbach et al., "Microscopy with Non-Diffracting Beams", FOM, 2009.
C. Dunsby, "Optically Sectioned Imaging by Oblique Plane Microscopy", Optics Express, Dec. 8, 2008, vol. 16, No. 25.
German-language Written Opinion (PCT/ISA/237) dated Jun. 5, 2012 (Six (6) pages).
German-language Office Action dated Jan. 13, 2012 (Four (4) pages).
International Search Report dated Jun. 5, 2012 with English translation (Eleven (11) pages).
International Preliminary Report on Patentability (PCT/IB/326, PCT/IB/338 & PCT/IB/373) dated Aug. 29, 2013, (eight (8) pages)+.

* cited by examiner

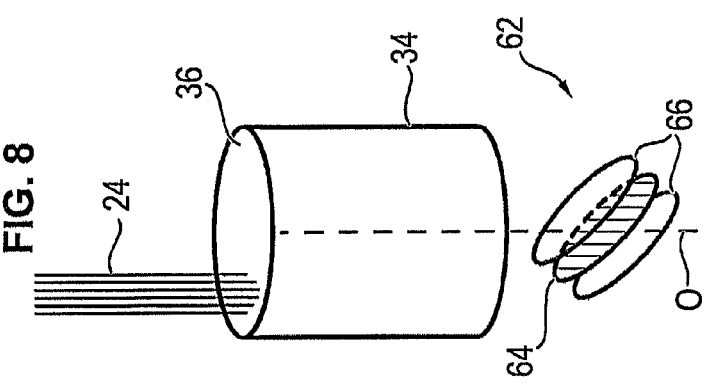
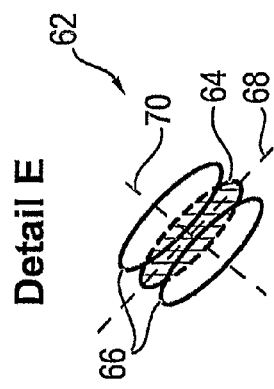
FIG. 8
Detail E

SCANNING MICROSCOPE, AND METHOD FOR LIGHT MICROSCOPY IMAGING OF A SPECIMEN

The invention relates to a scanning microscope having an illumination unit for emitting an illumination light beam, an objective for generating an elongated illumination focus in a specimen to be imaged, and a scanning apparatus for moving the illumination focus over a target region of the specimen to be illuminated by modifying the direction of incidence in which the illumination light beam is incident into an entrance pupil of the objective. The invention further relates to a method for light microscopy imaging of a specimen.

Scanning microscopes that are used, for example, in fluorescence microscopy to excite dyes with laser light to emit fluorescent radiation that is then sensed by a detector in order to image the specimen being investigated, are known from the existing art. Confocal scanning microscopes are used in particular in this sector of microscopy; in contrast to conventional light microscopes, these do not illuminate the entire specimen at a specific point in time, but instead generate a light spot, as a rule diffraction-limited, with which the specimen is scanned point by point. The light signals sensed by the detector in the individual specimen points are then assembled into an overall image of the specimen.

A confocal microscope of this kind usually comprises a so-called point scanner as a scanning apparatus, which directs the illumination light beam delivered by the illumination unit into the entrance pupil of the microscope objective. The microscope objective shapes the illumination light beam incident into its entrance pupil into a focused light distribution that is referred to hereinafter as an "illumination focus." The shape and size of the illumination focus depend on the optical properties, in particular the numerical aperture, of the objective. If the illumination light beam is incident centeredly and perpendicularly, i.e. along the optical axis, into the entrance pupil of the objective, the objective then generates an elongated illumination focus whose dimension transversely to the optical axis is less than along the optical axis. The illumination focus is then moved transversely to the optical axis in order to scan the specimen, by the fact that the point scanner, for example by way of a movable mirror arrangement, modifies the angle of incidence at which the illumination light beam is incident into the entrance pupil of the objective.

In order to perform three-dimensional imaging by means of a confocal microscope, the specimen must therefore be scanned point by point in the manner described above. Since this is relatively complex, a microscopy method referred to in the literature as selective plane illumination microscopy (SPIM) has recently been proposed in the literature. This method works with an illumination objective and a detection objective that are arranged at a 90-degree angle to one another. The illumination objective generates, in coaction with a cylindrical lens arranged in front of it, an approximately flat illumination light distribution that passes through the specimen along the optical axis of the illumination objective. A light distribution of this kind is often also referred to as a "light sheet" or "light plane." The target region of the specimen illuminated by this light sheet is imaged by the detection objective, whose optical axis extends perpendicular to the light sheet, onto a detection surface, e.g. a CCD. If the illuminating light sheet is then moved within the specimen to be imaged, layered images of the specimen can then be acquired with this arrangement.

In order to generate the thinnest possible light sheet, the illumination objective must have a correspondingly high numerical aperture, and the clear working distance of the illumination objective must be correspondingly large in order to avoid a collision with the detection objective. The numerical aperture of the illumination objective therefore defines the thickness of the light sheet, and thus the optical resolution along the optical axis of the detection objective.

In a modified SPIM method described in WO 2010/012980 A1, illumination and detection occur with one and the same objective. For this, the entrance pupil of the objective is decentrally underilluminated, i.e. the illumination light beam passes through a part of the entrance pupil that is offset transversely to the optical axis. A cylindrical lens arranged in front of the objective generates in the specimen an illuminating light sheet that is inclined with respect to the optical axis of the objective.

The target region of the specimen illuminated by this light sheet is then in turn imaged through the objective.

The devices described above each operate with a cylindrical lens in order to achieve the desired inclined illumination of the specimen. The use of such a cylindrical lens has disadvantages, however. For example, these devices are designed exclusively for inclined illumination by means of a light sheet, and do not enable any use deviating therefrom, for example point-by-point confocal scanning. It would also be desirable to be able to vary the spatial distribution of the light intensity of the light sheet generated for inclined illumination. This is not possible with a cylindrical lens.

DE 10 2005 007 756 A1 discloses a scanning microscope in which, in order to incline the illumination focus, the illumination light beam is directed onto a sub-region, offset from the center of the pupil, of the entrance pupil of the objective.

DE 10 2007 045 897 A1 discloses a microscope in which the light sheet is generated by means of a scanner.

For additional literature, reference is also made to A.H. Voie et al.: "Orthogonal-plane fluorescence optical sectioning: three-dimensional imaging of macroscopic biological specimens," Journal of Microscopy 170, 229-236 (1993); J. Huisken, J. Swoger, F. Del Bene, J. Wittbold, E. H. K. Stelzer: "Optical sectioning deep inside live embryos by selective plane illumination microscopy," Science 305, 1007 (2004); F. Fahrbach, A. Rohrbach, "Microscopy with non-diffracting beams," FOM 2009, Cracow; C. Dunsby, "Optically sectioned imaging by oblique plane mirror microscopy," Optics Express vol. 16, 25 (2008), DE 10 2005 027 077 A1; DE 44 16 558 C2; U.S. Pat. No. 5,952,668; WO 2006/127692 A2; DE 10 2006 021 317 B3; WO 2007/128434 A1; US 2009/0134342 A1; DE 10 2008 024 568 A1; US 2008/0032414 A1.

The object of the invention is to describe a scanning microscope, in particular a confocal scanning microscope, that makes possible, in simple fashion, flexible illumination of the specimen to be imaged.

The invention achieves this object, in a scanning microscope of the kind recited previously, in that in order to incline the illumination focus relative to the optical axis of the objective, the scanning apparatus directs the illumination light beam onto a sub-region, offset from the center of the pupil, of the entrance pupil; and in order to move the illumination focus over the target region to be illuminated, modifies the direction of incidence of the illumination light beam within that sub-region. The parallel offset of the plane of incidence with respect to the optical axis of the objective is within the range of approximately 4 to 96% of the radius of the entrance pupil.

The invention makes provision on the one hand to decentrally underilluminate the entrance pupil of the objective with the illumination light beam by directing the illumination light beam onto a sub-region of the entrance pupil offset from the pupil center. The underillumination of the entrance pupil, i.e.

the action of causing the illumination light beam not to pass through the entire area of the entrance pupil and thus of not using the full aperture, produces an expansion of the (previously elongated) illumination focus in both a longitudinal and a transverse direction. Because the illumination light beam is moreover incident eccentrically onto the entrance pupil, the illumination focus is inclined relative to the optical axis of the objective.

The illumination focus, expanded and inclined in this manner, can now be used to sequentially build up a light sheet illuminating the target region. This purpose is served by the scanning apparatus, which provides a corresponding scanning motion of the illumination light beam in the entrance pupil of the objective. This scanning motion corresponds to a tilting of the illumination light beam around a tilting point that is located in the region of the entrance pupil. This means that the illumination light beam, which is of course not a beam in the mathematical sense but instead a bundle of light beams, remains (at least approximately) stationary in the region of the entrance pupil, while at a distance from the entrance pupil, in the direction toward the scanning apparatus, it executes a kind of pivoting motion relative to a reference direction located parallel to the optical axis. The objective converts this tilting or pivoting motion of the illumination light beam into a corresponding motion of the inclined illumination focus transversely to the optical axis. The actual magnitude of the motion of the illumination focus in the specimen depends on the specific construction of the objective. It is essential, however, that according to the present invention, the tilting of the illumination light beam produced by the scanning apparatus is used to move the illumination focus within the target region of the specimen, and thus, so to speak, to build up a light sheet that illuminates the target region.

In contrast to the approaches known from the existing art, which work with a cylindrical lens in order to generate a light sheet, with the scanning microscope according to the present invention the light sheet is built up sequentially by means of the scanning apparatus by moving the illumination focus over the target region within a scanning period. In order to generate the light sheet, the scanning microscope according to the present invention thus makes use of the fact that the scan periods at which present-day scanning apparatuses can be operated are so short that they fall well below the detection cycles of light detectors that are usually used. Because, in the case of light sheet generation, only a line (in the X or Y direction) is being generated, the total illumination duration for the complete light sheet depends on the scan rate of the illumination scanner, i.e. of the scanning apparatus. Depending on the scanner type, this can be in the range from 1 Hz to several tens of kHz. The light detector (chiefly an area detector; CCD; CMOS, APD array, etc.) therefore "sees" the moving illumination focus as being unresolved in terms of time and therefore of space. Instead, it sees an uninterrupted light distribution in the form of the light sheet. By way of example, values for the scanning period are in a range from a few hundredths of a millisecond to 1 second, while the detection time for the entire light sheet plane (depending on the detector resolution, e.g. 512×512 pixels) is between a few milliseconds and seconds, provided there is certainty that the scanning period is shorter than the detection time.

Because a scanning apparatus that moves the illumination light beam is provided in any case in a conventional confocal scanning microscope, the invention makes possible particularly efficient generation of the illuminating light sheet. It is possible in particular to provide substantially one and the same microscope configuration for different applications. For example, in order to implement the application according to the present invention, in which inclined illumination of the specimen by means of a light sheet is performed, all that is necessary is to provide, in a confocal scanning microscope of inherently standard construction, for decentral underillumination of the entrance pupil of the objective. This can occur, for example, by means of an optical element that is introduced into the light path of the illumination light beam. If the scanning microscope then needs to operate again with point-type illumination, the optical element then simply needs to be removed again from the light path of the illumination light beam.

The scanning microscope according to the present invention makes it possible to acquire high-resolution sectional images of the specimen. For this, the specimen is scanned in steps with the light sheet. This scanning occurs by the fact that the objective and the specimen are moved along the optical axis relative to one another.

The scanning apparatus preferably modifies the direction of incidence of the illumination light beam in order to generate a light sheet, formed by the moving illumination focus, within a plane of incidence that is offset parallel to the optical axis of the objective. Assuming that the entrance pupil is of circular configuration, the aforementioned plane of incidence forms, in a plan view onto the entrance pupil, a straight line that intersects the circle defined by the pupil edge at two different points (in the manner of a secant), without crossing the center point of that circle. In the above-defined plan view, the illumination light beam then executes a tilting motion along that secant. The objective converts this tilting motion into a corresponding motion of the illumination focus along a straight line that extends parallel to the above-mentioned secant. The desired light sheet for illuminating the target region can thereby be generated in simple fashion.

In a further advantageous embodiment, the scanning apparatus comprises an optical offsetting element, arranged in the light path of the illumination light beam between the illumination unit and the objective, with which the plane of incidence of the illumination light beam is offset parallel to the optical axis of the objective. This offsetting element can be, for example, a glass wedge, a plane-parallel plate, an optical or photonic crystal, a spatial light modulator (SLM), a micromirror actuator (digital micromirror device, DMD), etc. Alternatively, it is also possible to arrange the scanning apparatus relative to the entrance pupil of the objective in such a way that the illumination light beam is incident decentrally in the desired fashion into the entrance pupil. It is also possible to trim the illumination light beam on one side in its light path before the scanning apparatus, for example using a stop, so that the desired decentral illumination of the entrance pupil is achieved. In a further alternative embodiment, optical elements that are in any case already present in the scanning microscope can be used to generate the desired beam offset. For example, an outcoupling beam splitter that is usually present in a scanning microscope, and that allows the illumination light beam to pass through toward the objective while reflecting the detected light deriving from the specimen in the direction of the light detector, can be constituted from a (for example, correspondingly coated) glass substrate whose thickness is dimensioned such that the desired beam offset, which is usually in a range of a few millimeters, is brought about.

The scanning apparatus preferably comprises a positioning element for introducing the optical offsetting element into and removing it from the light path of the illumination light beam. By means of such a positioning element, the offsetting element can be introduced as desired into the illumination light beam path and removed from it, for example in order thereby to switch between a usual confocal illumination and the inclined illumination according to the present invention using a light sheet. It is furthermore possible with such a positioning element to displace the offsetting element (of, for example, wedge-shaped configuration) incrementally into the light path of the illumination light beam so as thereby to bring about any desired decentering of the illumination light beam with respect to the objective.

In a further preferred embodiment, the scanning apparatus comprises an optical beam adjusting element, arranged in the light path of the illumination light beam between the illumination unit and the objective, for modifying the beam diameter of the illumination light beam emitted from the illumination unit. The beam adjusting element makes it possible to adjust the beam diameter of the illumination light beam, and thus the underlighting of the entrance pupil of the objective, as necessary in order to achieve the desired dimension of the illumination focus. Alternative embodiments are, however, also conceivable. For example, a confocal scanning microscope often comprises a beam-expanding optic in order to expand the illumination light beam delivered by the illumination unit in such a way that the entrance pupil of the objective is fully illuminated, and the full aperture is therefore used. If such an optic is present in any case in the scanning microscope, it can then also be used to correspondingly decrease the beam diameter in order to bring about the underlighting according to the present invention of the entrance pupil. The embodiments recited above are of course to be understood as being merely exemplifying. For example, stops or other optical elements can also be used to establish the desired beam diameter.

In a particularly preferred embodiment, the illumination light beam is assembled from an excitation light beam and a deexcitation light beam that are superimposed onto one another before entering the scanning apparatus. The objective correspondingly generates an excitation focus from the excitation light beam and a deexcitation focus from the deexcitation light beam, which are superimposed onto one another to yield the illumination focus. In the field of fluorescence microscopy, a deexcitation light beam of this kind can be used, for example in accordance with the so-called STED method, to increase the spatial resolution beyond the diffraction limit. In the STED method, fluorescent dyes that are used to mark individual regions of the specimen are deexcited in controlled fashion and in a manner known per se by the deexcitation light beam, and thus, so to speak, switched off, in order to increase the resolution capability. In the scanning microscope according to the present invention, by using the STED method the effectiveness of the illumination focus can be narrowed in order to increase the resolution, and the resulting light sheet can thus be made thinner, by the fact that the deexcitation light beam is superimposed onto the excitation light beam. Because the deexcitation light beam is superimposed onto the excitation light beam even before reaching the scanning apparatus, the two mutually superimposed light beams are tilted together by the scanning apparatus in the entrance pupil of the objective.

The deexcitation focus preferably has a spatial light intensity distribution that has a minimum in a plane in which the illumination focus assembled from the excitation focus and the deexcitation focus is moved in order to generate a light sheet, and a respective maximum on either side of that plane. Whereas with conventional application of the STED method the deexcitation focus has an annular shape in cross section, the embodiment recited here provides for an deexcitation focus that has in cross section (above and below the plane in which the illumination focus is moved in order to generate the light sheet) two intensity maxima and a minimum between those maxima. This cross-sectional intensity profile is preferably of symmetrical embodiment, having two maxima of identical magnitude and a zero point, as minimum, located between them.

This advantageous embodiment exploits the fact that a STED deexcitation in the plane in which the illumination focus is moved in order to generate the light sheet is not necessary, and in fact is undesirable. With the approach according to the present invention, the intention is to generate a light sheet that has the largest possible area and at the same time is as thin as possible, so that optical sectional images of high spatial resolution can be acquired. The area of the light sheet is defined here by the length of the moving illumination focus, while the sheet thickness is defined by the dimension of the illumination focus transversely to the plane in which the illumination focus is moved. The deexcitation focus described above is then shaped specifically so that it decreases the excitation effectiveness of the excitation focus only in the direction of the transverse focus dimension, but not in the direction of the longitudinal focus dimension.

To generate the deexcitation focus superimposed on the excitation focus, a phase plate, for example, which adjusts the spatial intensity distribution of the deexcitation light beam in accordance with the desired shape of the deexcitation focus, is arranged in the light path of the deexcitation light beam. This desired shape of the deexcitation focus can be generated with less technical outlay, in the form of a simple phase plate, than is the case in the usual application of the STED method in which the deexcitation focus must be of annular configuration. The phase plate is arranged in the light path of the deexcitation light beam preferably in front of the scanning apparatus. It can, however, also be embodied immediately in front of the entrance pupil of the objective, e.g. on an outcoupling beam splitter arranged in front of the objective. It is likewise possible to arrange the phase plate directly in the objective.

The scanning microscope according to the present invention preferably encompasses an element for varying the intensity of the illumination light beam within a scanning period during which the illumination focus is moved over the target region. This configuration exploits the fact that the light sheet illuminating the target region is spanned sequentially by the moving illumination focus. It is thereby possible to implement modulated or structured illumination of the target region. For this, the intensity of the illumination light beam is varied within the scanning period in which the illumination focus scans the target region. The intensity of the illumination light beam can thus be adjusted as desired at any point in time within the scanning period, and thus at any location in the target region. An acousto-optical tunable filter (AOTF), acousto-optical modulator (AOM), or electro-optical modulator (EOM) can be used, for example, as an element that varies the intensity of the illumination light beam within the scanning period.

In a further preferred embodiment, the scanning microscope encompasses a detection optic having a first sub-optic for intermediate imaging of an image, arranged at an inclination to the optical axis of the first sub-optic and generated by the objective, of the target region illuminated by the inclined illumination focus; and a second sub-optic for imaging the intermediate image, generated by the first sub-optic, onto a detection surface that is arranged parallel to the intermediate image. The two sub-optics ensure erection of the target region imaged by the objective under the inclined illumination. Such image erection is, however, also possible in a different manner, for example using a so-called Scheimpflug arrangement.

A CCD, a sCMOS, or other area detectors, such as an APD array, can be used, for example, as a detection surface on which the erected image of the target region is ultimately generated.

According to a further aspect of the invention, a method for light microscopy imaging of a specimen, having the features of Claim 14, is provided.

In a preferred embodiment of the method according to the present invention, the intensity of the illuminating light beam is varied within a scanning period during which the illumination focus is moved over the target region. It is possible in particular to image different observation volumes by alternatingly switching the excitation light beam and/or deexcitation light beam in and out. If the excitation light beam and/or deexcitation light beam are switched in and out on a microsecond scale, different volumes can then be detected, for example, column by column by appropriate synchronization with the light detector (if it is assumed that the detection surface of the light detector is made up of rows and columns).

The method according to the present invention can advantageously be used in localization microscopy. Switchable fluorescing proteins, fluorescent dyes such as ATTO, Alexa, rhodamine derivatives, fluorescein derivatives, nanocrystals, etc. are suitable as fluorescent dyes. Using the inclined illumination, the fluorescing components either can be activated or can be driven to saturation. Metered illumination ensures that single-molecule detection is possible. The sites of the fluorescent dyes can be determined by determining the center points of the detected photons.

The method according to the present invention can be used particularly profitably for small-animal imaging, for example fluorescence imaging of fish, since the specimens used in this case are easily accessible.

The invention will be further explained below with reference to the Figures, in which:

FIG. 8 is a schematic depiction illustrating the superimposition according to the present invention of the illumination focus onto the excitation focus.

FIG. 1 is a schematic depiction of a confocal scanning microscope 10 as a first exemplifying embodiment. Be it noted that components of scanning microscope 10 that are not essential for an understanding of the subject matter of the invention have been omitted from the depiction in FIG. 1.

Figure 1:
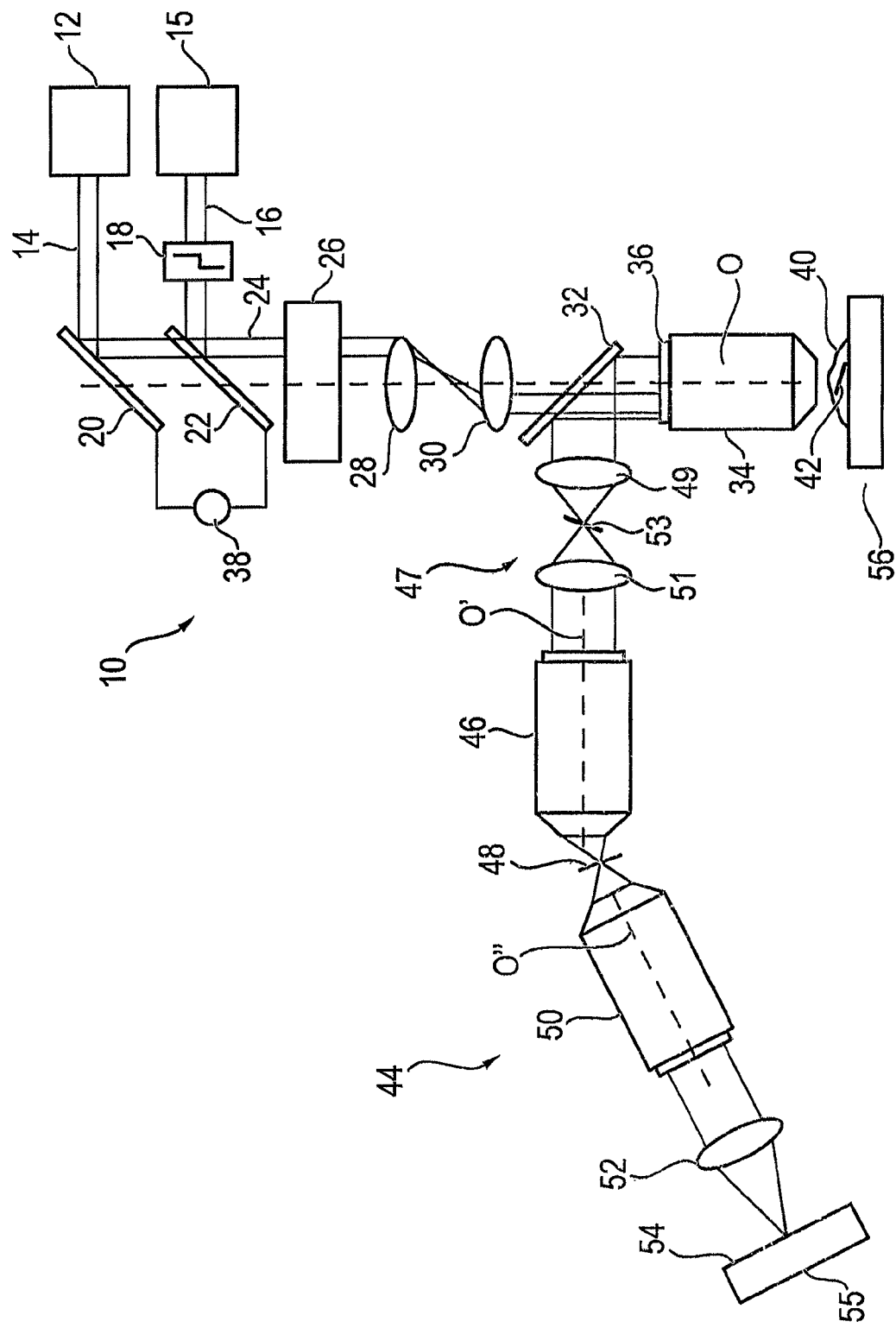
FIG. 1 shows a confocal scanning microscope as a first exemplifying embodiment.

Scanning microscope 10 constitutes a confocal fluorescence microscope that is designed to achieve a spatial resolution exceeding the diffraction limit using the STED method known per se. Scanning microscope 10 accordingly encompasses a first laser light source 12, hereinafter referred to as an "excitation light source," as well as a second laser light source 15, hereinafter referred to as a "deexcitation light source." Excitation light source 12 emits an excitation light beam 14 whose wavelength is selected so that the fluorescent dyes used in the applicable microscopy method are stimulated to emit fluorescent radiation. Deexcitation light source 15, on the other hand, emits a deexcitation light beam 16 which becomes superimposed onto excitation light beam 14 in a manner described below, and whose wavelength is selected so that the fluorescent dyes illuminated by the excitation light beam become deexcited by stimulated emission and thereby, so to speak, switched off. Deexcitation light beam 16 emitted by deexcitation light source 15 passes through a phase plate 18 which serves to establish a desired intensity profile of deexcitation light beam 16.

Excitation light beam 14 is incident onto a mirror 20 and is reflected at it toward a beam splitter 22. Beam splitter 22 is embodied so that it allows excitation light beam 14 to pass, while it reflects deexcitation light beam 16 that is incident onto it. Excitation light beam 14, and deexcitation light beam 16 influenced in terms of its intensity profile by phase plate 18, are thereby superimposed onto one another. The light beam formed from the two light beams 14 and 16 superimposed onto one another will be referred to hereinafter as illumination light beam 24.

Illumination light beam 24 strikes a galvano mirror arrangement 26, depicted entirely schematically in FIG. 1, which serves to deflect the illumination light beam in such a way that the latter executes a scanning motion described in further detail below. Illumination light beam 24 then passes through a scanning lens 28, a tube lens 30, and a beam splitter 32, and lastly strikes an objective 34.

As the illumination light beam path schematically depicted in FIG. 1 shows, illumination light beam 24 entering objective 34 does not completely illuminate an entrance pupil (labeled 36 in FIG. 1) of objective 34. This means that illumination light beam 24 passes through only a sub-region of entrance pupil 36 and thus does not use the full aperture of objective 34. In addition, illumination light beam 24 entering objective 34 is offset with respect to the optical axis (labeled O in FIG. 1). Illumination light beam 24 is thus directed onto objective 34 in such a way that it decentrally underilluminates its entrance pupil 36.

This decentral underillumination of entrance pupil 36 with illumination light beam 24 is achieved in the present exemplifying embodiment by the fact that illumination light beam 24 reflected from galvano mirror arrangement 26 is incident onto an edge region of scanning lens 28 with a parallel offset relative to optical axis O. As a result of this parallel offset, illumination light beam 24 emerging from scanning lens 28 firstly crosses optical axis O and is then incident again onto an edge region of tube lens 30, this edge region being located on the other side of optical axis O from that edge region of scanning lens 28 through which light passes. From tube lens 30, illumination light beam 24 then enters entrance pupil 36 of objective 34 with a parallel offset with respect to optical axis O. Tube lens 30 deflects illumination light beam 24 in such a way that the latter is incident into entrance pupil 36 of objective 34 with a parallel offset relative to optical axis O.

In the exemplifying embodiment shown in FIG. 1, mirror 20 and beam splitter 22 already ensure that illumination light beam 24, assembled from excitation light beam 14 and deexcitation light beam 16, are incident onto galvano mirror arrangement 26 with a parallel offset relative to optical axis O. This parallel offset can be adjusted by means of an adjusting element 38. For this, adjusting element 38 displaces mirror 20 and beam splitter 22 as a unit transversely to optical axis O.

Components 20, 22, 26, 28, 30, and 38 explained above constitute a scanning apparatus that serves to tilt illumination light beam 24 in entrance pupil 36 of objective 34, as described below in detail. Objective 34 reshapes illumination light beam 24, entering its entrance pupil 36, into an illumination focus (not shown in FIG. 1) that is moved by the tilting motion of illumination light beam 24, within a scanning period of the scanning apparatus, over a target region of a specimen 40 to be imaged. The motion of the illumination focus causes generation of a light sheet that, because of the decentral entry of illumination light beam 24 into entrance pupil 36 of objective 34, is inclined with respect to optical axis O. This light sheet is labeled 42 in the schematic depiction of FIG. 1.

The fluorescent radiation deriving from the target region, illuminated with light sheet 42, of specimen 40 is in turn captured by objective 34. The fluorescent radiation is reflected at beam splitter 32 toward a detection optic labeled generally as 44 in FIG. 1. Detection optic 44 encompasses a first detection objective 46 that is located after a tube lens system 47 that is made up of two tube lenses 49, 51. Tube lens 49 is associated with objective 34, while tube lens 51 is associated with first detection objective 46. Tube lens 49 generates, in coaction with objective 34, a first intermediate image 53. The optical axis (labeled O' in FIG. 1) of first detection objective 46 extends perpendicular to optical axis O of objective 34. Because the target region illuminated with light sheet 42 is arranged at an inclination with respect to optical axis O of objective 34, first intermediate image 53 is also located at an inclination with respect to optical axis O' of first detection objective 46. First detection objective 46, in coaction with tube lens 51, images first intermediate image 53 into a second intermediate image 48 that is likewise arranged at an inclination with respect to optical axis O'.

Detection optic 44 further encompasses a second detection objective 50 that images second intermediate image 48 via a tube lens 52 onto a detection surface 54 of a light detector 55. The optical axis (labeled O" of second detection objective 50 is perpendicular to second intermediate image 48 and perpendicular to detection surface 54. Thanks to the coaction of the two detection objectives 46 and 50, an upright image of the inclined target region of specimen 40, illuminated with light sheet 42, can thereby be generated, largely without aberrations, on detection surface 54.

In order to acquire a series of high-resolution sectional images of specimen 40, in the present exemplifying embodiment a specimen slide 56 on which specimen 40 is arranged is moved successively along or transversely to optical axis O. A high-resolution three-dimensional image of specimen 40 can be made in this fashion.

Figure 2:
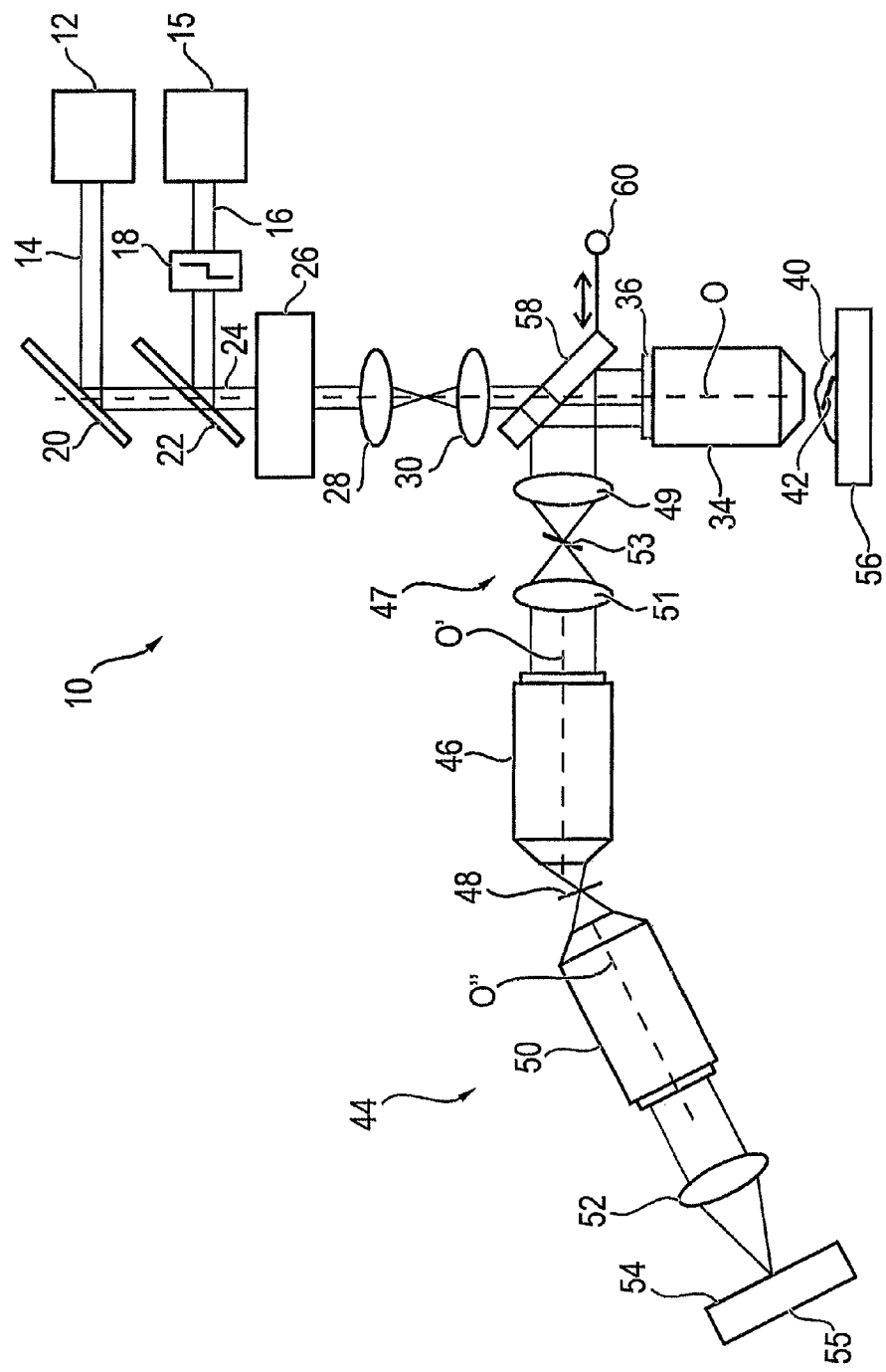
FIG. 2 shows an embodiment modified as compared with the scanning microscope of FIG. 1, as a second exemplifying embodiment.

FIG. 2 shows a modified embodiment as a second exemplifying embodiment. In this second exemplifying embodiment, the parallel offset of illumination light beam 24 with respect to optical axis O of objective 34 prior to entering entrance 36 is brought about in a different manner than in the first exemplifying embodiment. In the embodiment according to FIG. 2, illumination light beam 24 propagates on optical axis O as far as a beam splitter 58. Unlike beam splitter 32 of FIG. 1, beam splitter 58 is constituted from a comparatively thick, plane-parallel substrate that, upon passage of illumination light beam 24, provides the desired parallel offset with respect to optical axis O. Beam splitter 59 can be displaced transversely to optical axis O by way of a positioning element 60 in order to vary the parallel offset.

Figure 3:
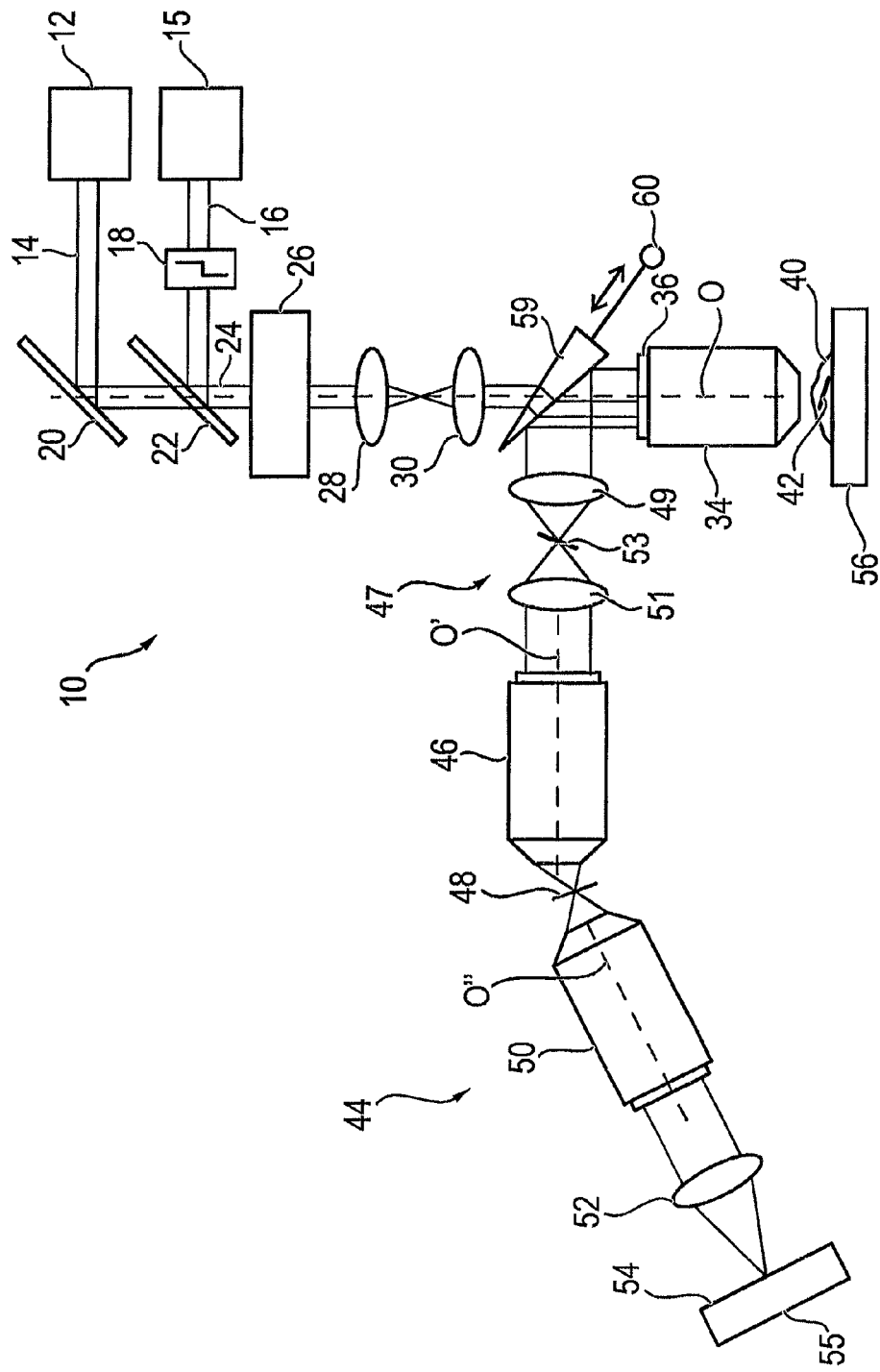
FIG. 3 shows an embodiment modified as compared with the scanning microscope of FIG. 2, as a third exemplifying embodiment.

FIG. 3 shows a third exemplifying embodiment. The third exemplifying embodiment differs from the embodiment shown in FIG. 2 in that beam splitter 58 constituted from a plane-parallel substrate is replaced by a wedge-shaped beam splitter 59. In this exemplifying embodiment as well, beam splitter 59 is shiftable by means of positioning element 60 in order to produce the desired parallel offset of illumination light beam 24.

The manner in which light sheet 42 is generated according to the present invention will be explained in detail below with reference to FIGS. 4 to 8. Be it noted in this regard that FIGS. 4 to 8 are entirely schematic depictions that are intended to facilitate comprehension of the invention. In addition, in order to facilitate comprehension, it will firstly be assumed for the situation shown in FIGS. 4 to 7 that illumination light beam 24 is constituted only by excitation light beam 14, i.e. that superimposition with deexcitation light beam 16 has not yet occurred.

Figure 4:
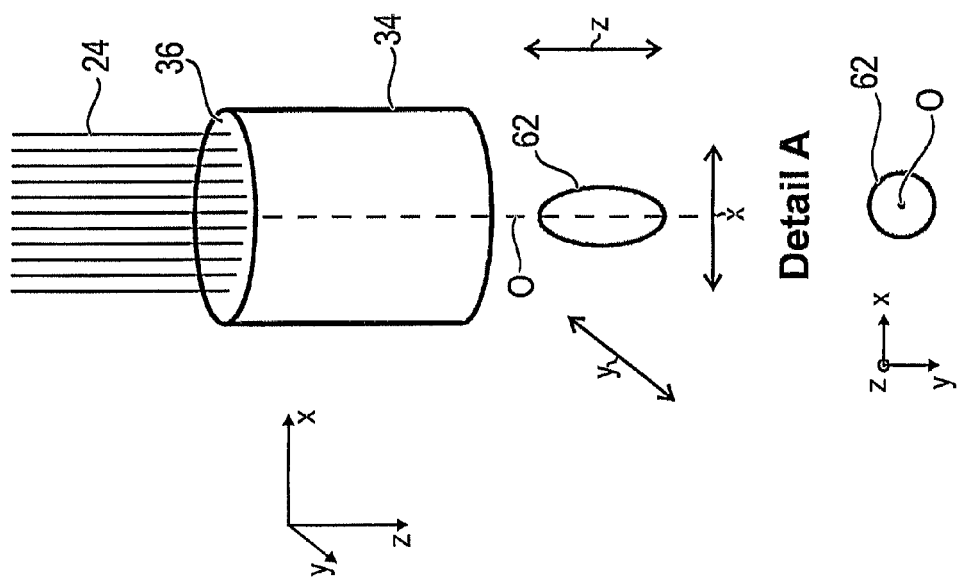
FIG. 4 is a schematic depiction illustrating complete illumination of the entrance pupil of an objective with the illumination light beam, as utilized in conventional confocal scanning microscopy.

FIG. 4 firstly illustrates the situation, typical of conventional confocal point-type scanning, in which the ray bundle formed by illumination light beam 24 uses the full objective aperture, i.e. passes through the entire area of entrance pupil 36 of objective 34. In FIG. 4, illumination light beam 24 is oriented parallel to optical axis O. In this case objective 36 generates a focused light distribution whose dimension is greater along optical axis O than transversely to optical axis O. This light distribution, referred to in the present Application as an "illumination focus," is labeled 62 in FIG. 4.

For the explanations that follow, reference will be made in each case to a coordinate system whose X axis is oriented horizontally in the drawing plane and whose Z axis is oriented vertically in the drawing plane, while the Y axis points out of the drawing plane. With this definition, entrance pupil 36 is arranged parallel to the X-Y plane, while optical axis O extends parallel to the Z axis. FIG. 4 further depicts, at A, a plan view of illumination focus 62 in the direction of the Z axis. In this conventional arrangement, illumination focus 62 is circular in plan view.

Figure 5:
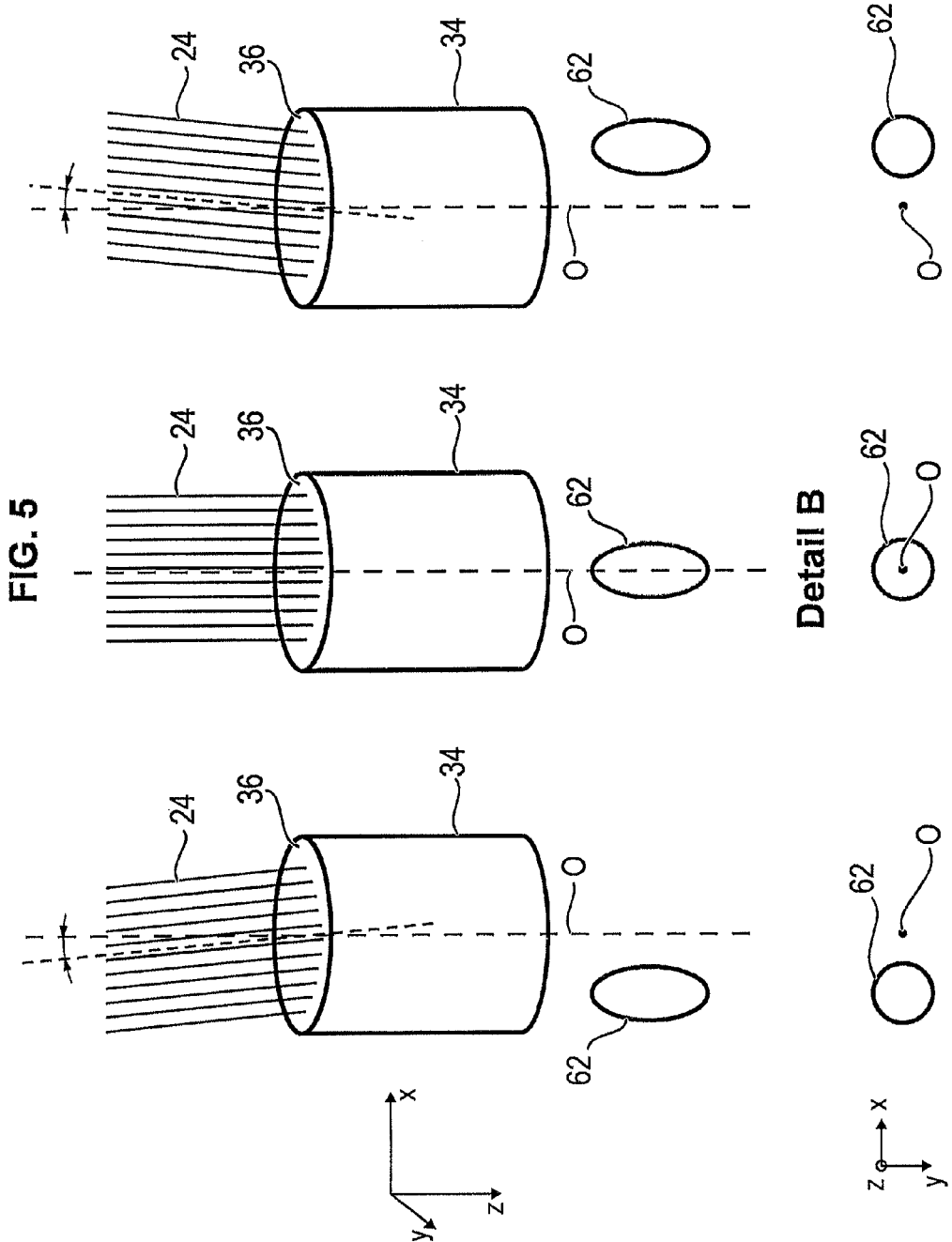
FIG. 5 is a schematic depiction illustrating scanning with the illumination light beam, utilized in conventional confocal scanning microscopy.

FIG. 5 now shows how the location of illumination focus 62 changes when illumination light beam 24 in entrance pupil 36 is tilted by the scanning apparatus described above. For the situation shown in FIG. 5, it is assumed that the main beam of the ray bundle formed by illumination light beam 24 is tilted in a plane of incidence that lies parallel to the X-Z plane. In addition, illumination light beam 24 is still assumed to be passing through the entire area of entrance pupil 36, i.e. completely illuminating entrance pupil 36.

Illumination light beam 24 is tilted in the plane of incidence in such a way that it changes its direction of incidence relative to optical axis O. This change in the direction of incidence is converted by objective 34 into a shift of illumination focus 62 transversely to optical axis O. In the situation shown in FIG. 5, this motion takes place along the X axis. Because illumination light beam 24 is still passing through the entire area of entrance pupil 36, illumination focus 62 remains oriented with its longitudinal dimension parallel to optical axis O. This is also apparent in the plan views shown at B in FIG. 5, in which illumination focus 62 is still circular.

Figure 6:
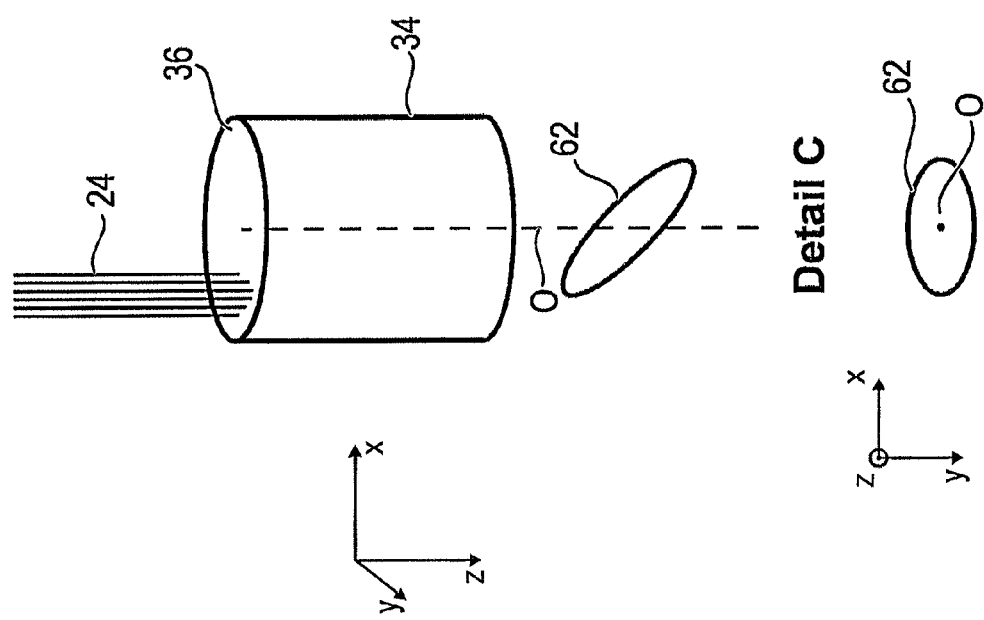
FIG. 6 is a schematic depiction illustrating underillumination according to the present invention of the entrance pupil with the illumination light beam.

FIG. 6 depicts the underillumination according to the present invention of entrance pupil 36. As is evident from FIG. 6, illumination light beam 24 passes through only a sub-region of entrance pupil 36, this sub-region being arranged decentrally, i.e. being offset out of the center of the pupil transversely to optical axis O. This decentering of illumination light beam 24 in entrance pupil 36 causes illumination focus 62 to be inclined relative to optical axis O. This is also evident in the plan view shown at C, in which illumination focus 62 is no longer circular but instead is longer in the direction of the X axis than in the direction of the Y axis. The underillumination of illumination light beam 24 also causes an expansion of illumination focus 62, i.e. illumination focus 62 is larger overall than when entrance pupil 36 is completely illuminated.

Figure 7:
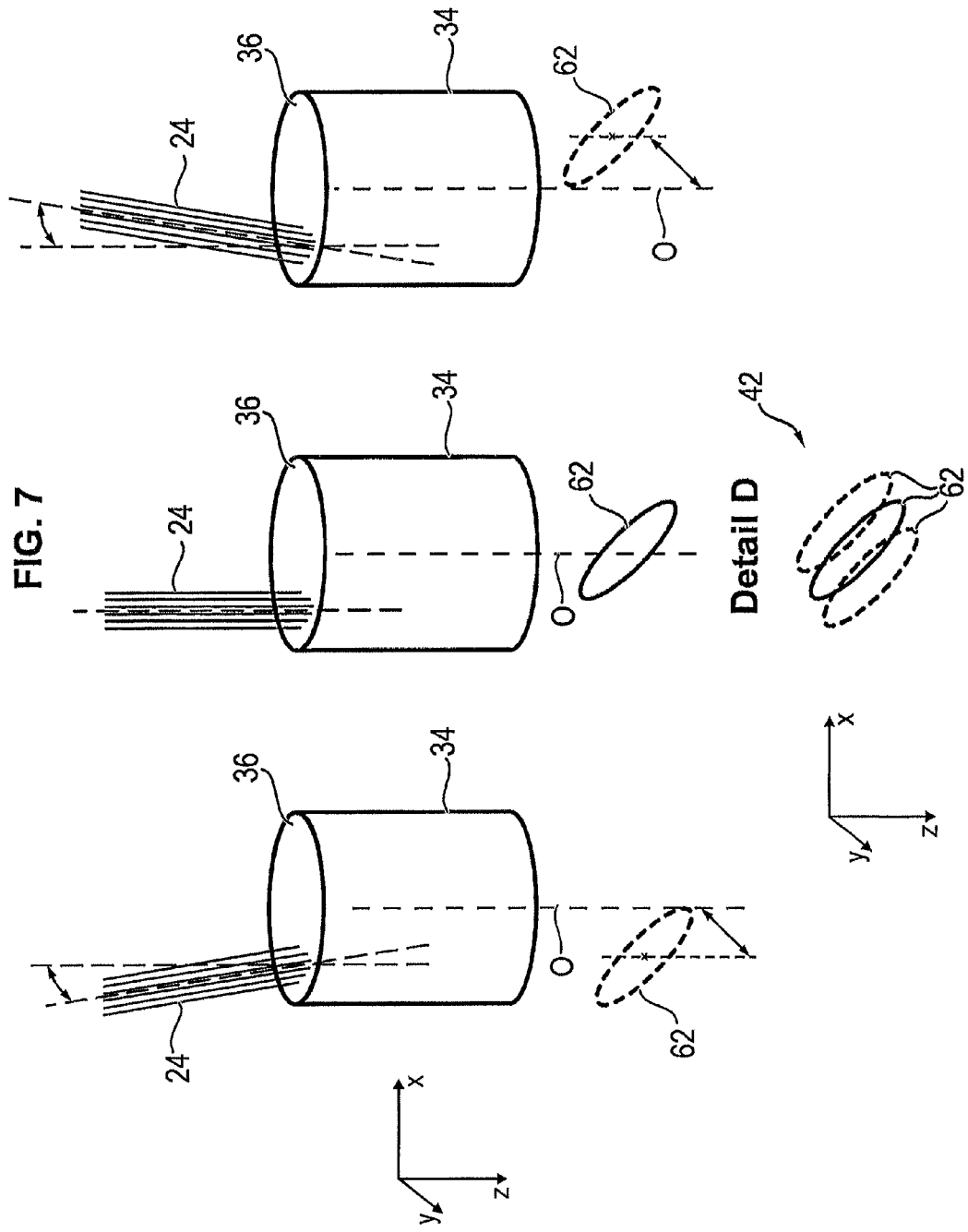
FIG. 7 is a schematic depiction illustrating scanning according to the present invention by tilting the illumination light beam that is underilluminating the entrance pupil.

FIG. 7 now shows the situation in which illumination light beam 24 that is decentrally underilluminating entrance pupil 36 becomes tilted in entrance pupil 36. For the situation shown in FIG. 7, it is to be assumed that the main beam of the ray bundle forming illumination light beam 24 becomes tilted in a plane of incidence that is parallel to optical axis O and lies parallel to the X-Z plane. This means that illumination light beam 24 in FIG. 7 is tilted out of and into the drawing plane.

This tilting of illumination light beam 24 is converted by objective 34 into a corresponding shift of the inclined illumination focus 62 along the Y axis. Illumination focus 62 is thus shifted out of and into the drawing plane in FIG. 7. This is illustrated again in FIG. 7 at D.

The motion sequence of illumination focus 62 shown in FIG. 7 under D clearly indicates how light sheet 42 is built up by moving illumination focus 62 within a scanning period. A prerequisite for this is that the scanning period in which illumination focus 62 is moved over the entire target region is shorter than the detection time that light detector 54 works with for image generation. The result is that light detector 54 senses the moving illumination focus 62 as being unresolved in time and therefore in space. Instead it senses an uninterrupted or continuous light distribution in the form of light sheet 42.

FIG. 8 now shows the situation in which illumination light beam 24 is formed from a superimposition of excitation light beam 14 and deexcitation light beam 16. Objective 34 correspondingly generates an excitation focus 64 as well as a deexcitation focus 66, the superimposition of which results in illumination focus 62. Excitation focus 64 corresponds in terms of shape to illumination focus 62 shown in FIGS. 5 and 6.

Deexcitation focus 66 is depicted in FIG. 8 at E, again in a section parallel to the X-Z plane. As is clear in particular from this depiction, deexcitation focus 66 has a spatial light intensity distribution in which the light intensity is equal to zero in the plane in which illumination focus 62 made up of excitation focus 64 and deexcitation focus 66 is moved, while it exhibits a respective maximum on either side of that plane. The motion plane recited above is labeled 68 in FIG. 7. It lies parallel to a plane which contains the Y axis and whose line intersecting the X-Z plane forms an angle with the X axis. That angle depends on the maximum opening angle of objective 34 that is used, and on the expansion and decentering of illumination light beam 24.

The fact that excitation focus 64 is overlaid by deexcitation focus 66 above and below said motion plane 68 causes the excitation effectiveness of excitation focus 62 to be reduced above and below motion plane 68. That portion of the excitation focus that is effective for excitation is indicated with hatching at E in FIG. 8.

The direction in which excitation focus 62 becomes, so to speak, constricted is indicated by a line 70 in FIG. 8. This constriction direction 70 is perpendicular to motion plane 68. The superimposition of excitation focus 64 and deexcitation focus 66 causes the excitation-effective light sheet 42 to become, as it were, thinner, with the result that the spatial resolution is increased.

The generation of light sheet 42 as described above offers the capability of effecting modulated or structured illumination of the target region of specimen 40. It is thus possible to vary the light intensity of excitation light beam 14 and/or of deexcitation light beam 16 within a scanning period as desired, for example by means of an AOTF (not shown in the Figures). By alternatingly switching excitation light beam 14 and/or deexcitation light beam 16 in and out, it is possible to image different observation volumes. If excitation light beam 14 and/or deexcitation light beam 16 are switched in and out on a microsecond scale, then by appropriate synchronization with light detector 55, for example, different volume elements can be detected column by column (if it is assumed that detection surface 55 of light detector 54 is made up of rows and columns).

PARTS LIST

10 Scanning microscope
12 Excitation light source
14 Excitation light beam
15 Deexcitation light source
16 Deexcitation light beam
18 Phase plate
20 Mirror
22 Beam splitter
24 Illumination light beam
26 Galvano mirror arrangement
28 Scanning lens
30 Tube lens
32 Beam splitter
34 Objective
36 Entrance pupil
38 Positioning element
40 Specimen
42 Light sheet
44 Detection optic
46 First detection objective
47 Tube lens system
48 Intermediate image
49 Tube lens
50 Second detection objective
51 Tube lens
52 Tube lens
53 Intermediate image
54 Detection surface
55 Light detector
56 Specimen slide
58 Beam splitter
60 Positioning element
62 Illumination focus
64 Excitation focus
66 Deexcitation focus
68 Motion plane
70 Constriction direction
O, O', O" Optical axes

The invention claimed is:

1. A scanning microscope for use in single-plane illumination, comprising:
   an illumination unit for emitting an illumination light beam,
   an objective for generating an elongated illumination focus in a specimen to be imaged, and
   a scanning apparatus for moving the illumination focus over a target region of the specimen to be illuminated by modifying the direction of incidence in which the illumination light beam is incident into an entrance pupil of the objective,
   wherein the scanning apparatus directs the illumination light beam onto a sub-region of the entrance pupil offset from the pupil center in order to incline the illumination focus relative to the optical axis (O) of the objective, and modifies the direction of incidence of the illumination light beam within that sub-region in order to move the illumination focus over the target region to be illuminated, and wherein the same objective that generates the illumination focus also serves as observation objective and images the specimen illuminated by the moved illumination focus.

2. The scanning microscope according to claim 1, wherein the scanning apparatus modifies the direction of incidence of the illumination light beam in order to generate a light sheet, formed by the moving illumination focus, within a plane of incidence that is offset parallel to the optical axis (O) of the objective.

3. The scanning microscope according to claim 2, wherein the sub-region of the entrance pupil through which the illumination light beam passes occupies approximately 0.1% to 50% of the total area of the entrance pupil, and the parallel offset of the plane of incidence with respect to the optical axis (O) of the objective is within the range of approximately 4 to 96% of the radius of the entrance pupil.

4. The scanning microscope according to claim 2, wherein the scanning apparatus comprises an optical offsetting element, arranged in the light path of the illumination light beam between the illumination unit and the objective, with which the plane of incidence of the illumination light beam is offset parallel to the optical axis (O) of the objective.

5. The scanning microscope according to claim 4, wherein the optical offsetting element is of wedge-shaped configuration.

6. The scanning microscope according to claim 4, wherein the scanning apparatus comprises a positioning element for introducing the optical offsetting element into and removing it from the light path of the illumination light beam.

7. The scanning microscope according to claim 1, wherein the scanning apparatus comprises at least one movable mirror that reflects the illumination light beam emitted from the illumination unit into the sub-region of the entrance pupil offset from the pupil center, and comprises a drive with which the mirror is movable in order to modify the direction of incidence of the illumination light beam.

8. The scanning microscope according to claim 7, wherein the mirror of the scanning apparatus is arranged at an offset with respect to the optical axis (O) of the objective.

9. The scanning microscope according to claim 1, wherein the scanning apparatus comprises an optical beam adjusting element, arranged in the light path of the illumination light beam between the illumination unit and the objective, for modifying the beam diameter of the illumination light beam emitted from the illumination unit.

10. The scanning microscope according to claim 1, wherein the illumination light beam is assembled from an excitation light beam and a deexcitation light beam that are superimposed onto one another before entering the scanning apparatus; and the objective generates an excitation focus from the excitation light beam and a deexcitation focus from the deexcitation light beam, which are superimposed onto one another to yield the illumination focus.

11. The scanning microscope according to claim 10, wherein the deexcitation focus has a spatial light intensity distribution that has a minimum in a plane in which the illumination focus assembled from the excitation focus and the deexcitation focus is moved in order to generate a light sheet, and a respective maximum on either side of that plane.

12. The scanning microscope according to claim 11, characterized by a phase plate, arranged in the light path of the deexcitation light beam, for adjusting the spatial intensity distribution of the deexcitation focus superimposed on the excitation focus.

13. The scanning microscope according to claim 1, characterized by an element for varying the intensity of the illumination light beam within a scanning period during which the illumination focus is moved over the target region.

14. The scanning microscope according to claim 1, characterized by a detection optic having a first sub-optic for intermediate imaging of an image, arranged at an inclination to the optical axis (O') of the first sub-optic and generated by the objective, of the target region illuminated by the inclined illumination focus; and a second sub-optic for imaging the intermediate image, generated by the first sub-optic, onto a detection surface that is arranged parallel to the intermediate image.

15. A method for light microscopy imaging of a specimen using single-plane illumination, the method comprising:
emitting an illumination light beam,
generating an elongated illumination focus in the specimen to be imaged by means of an objective,
moving the illumination focus over a target region of the specimen to be illuminated by modifying the direction of incidence in which the illumination light beam is incident into an entrance pupil of the objective,
wherein the illumination light beam is directed onto a sub-region of the entrance pupil offset from the pupil center in order to incline the illumination focus relative to the optical axis (O) of the objective, and the direction of incidence of the illumination light beam is modified within that sub-region in order to move the illumination focus over the target region to be illuminated, and
observing and imaging the specimen illuminated by the moved illumination focus by means of the same objective.

16. The method according to claim 15, wherein the direction of incidence of the illumination light beam is modified within a plane of incidence that is offset parallel to the optical axis (O) of the objective in order to generate a light sheet formed by the moving illumination focus.

17. The method according to claim 15, wherein the illumination light beam is assembled from an excitation light beam and a deexcitation light beam; and an excitation focus is generated from the excitation light beam and a deexcitation focus is generated from the deexcitation light beam, which are superimposed on one another to yield the illumination focus.

18. The method according to claim 17, wherein the spatial intensity distribution of the deexcitation focus is adjusted in such a way that it has a minimum in a plane in which the illumination focus assembled from the excitation focus and the deexcitation focus is moved in order to generate a light sheet, and a respective maximum on either side of that plane.

19. The method according to claim 15, wherein the intensity of the illumination light beam is varied within a scanning period during which the illumination focus is moved over the target region.

20. The method according to claim 19, wherein the excitation light beam and/or the deexcitation light beams are alternatingly switched on and off.

* * * * *